Figure 1A:
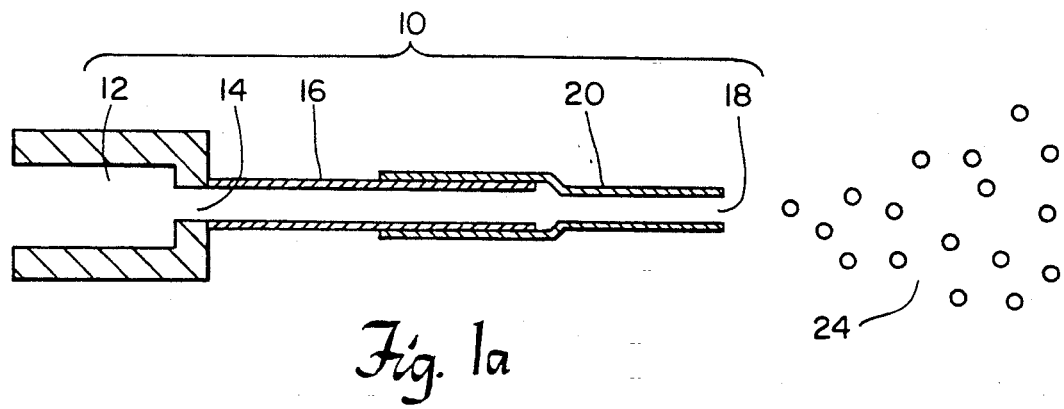

United States Patent [19]
Wittmer et al.

[11] Patent Number: 5,223,226
[45] Date of Patent: Jun. 29, 1993

[54] INSULATED NEEDLE FOR FORMING AN ELECTROSPRAY

[75] Inventors: Douglas P. Wittmer, Upton, Mass.; Michael J. Tomany, North Grosvenordale; Joseph A. Jarell, Newton Highlands, Mass.

[73] Assignee: Millipore Corporation, Bedford, Mass.

[21] Appl. No.: 868,825

[22] Filed: Apr. 14, 1992

[51] Int. Cl.⁵ .................... B01L 3/02; G01N 33/00; B01D 59/44
[52] U.S. Cl. .................... 422/100; 422/68.1; 204/180.1; 204/299 R; 250/281; 250/288; 604/187
[58] Field of Search .................... 250/288, 281; 204/180.1, 299 R; 422/100, 68.1; 604/187

[56] References Cited

U.S. PATENT DOCUMENTS

| | | | |
|---|---|---|---|
| 4,531,056 | 7/1985 | Labowsky et al. | 250/288 |
| 4,748,043 | 5/1988 | Sever et al. | 427/30 |
| 4,842,701 | 6/1989 | Smith et al. | 204/180.1 |
| 4,867,947 | 9/1989 | Andresen et al. | 422/70 |
| 4,885,076 | 12/1989 | Smith et al. | 204/299 R |

*Primary Examiner*—James C. Housel
*Assistant Examiner*—N. Bhat
*Attorney, Agent, or Firm*—Andrew T. Karnakis; Paul J. Cook

[57] ABSTRACT

An electrically insulated needle tip is provided for forming an electrospray from a solution containing a solute sample. The insulated needle tip is positioned between an upstream electrode and a downstream counterelectrode. The solution passes through the needle, emerges from the insulated tip and is converted to an electrospray under the influence of an electric field generated between the electrode and the counterelectrode.

10 Claims, 5 Drawing Sheets ns this invention relates to an electrically insulated needle tip apparatus for producing an electrospray formed from a sample solution. More particularly this invention relates to an electrically insulated needle tip apparatus for forming an electrospray which is converted to an ionic stream for analysis.

A liquid flowing through a capillary jet or orifice may be converted to a spray of small charged droplets (of the order of 1 μm is diameter) by applying a strong electric field to the liquid as it merges from the tip of the capillary. For a sufficiently high applied field, the electrostatic stress imposed by the field and the surface-induced electrical charge is sufficient to overcome the surface tension forces on the liquid. Breaking apart into a large number of small charged droplets is a way for the liquid to disperse the charge and reach a lower total energy state. This process of forming a spray is commonly known as electrospray.

At the present time apparatus are available for forming an electrospray of a sample solution such as a liquid stream effluent from a liquid chromatography separation step and subsequently analyzing the electrospray with a mass analyzer such as a quadrupole mass spectrometer, an ion trap mass spectrometer, a timeof-flight mass spectrometer or a magnetic sector mass spectrometer or the like.

In a liquid chromatograph, a stream of solvent, containing a mixture of chemical species in solution, is passed by elevated pressure through a chromatographic column. The column is so designed that it separates the mixture, by differential retention on the column, into its component species. The different species then emerge from the column as distinct bands in the solvent stream, separated in time. Coupling the output of a liquid chromatograph to a mass spectrometer via an electrospray interface gives the analyst a powerful tool since it can provide molecular weight and structural information about the separated species as they emerge from the liquid chromatograph.

At the present time, electrically conductive needles, typically formed of stainless steel are utilized for passage of a liquid sample and from which emerges an electrospray under the appropriate electrical field conditions. Needles of similar construction are utilized in an ion spray process which is a form of an electrospray process in which the liquid is nebulized by a turbulent flow of gas such as nitrogen. The use of electrically conductive needles permits only a narrow voltage operating range. In order to obtain a sufficiently high field strength to produce an electrospray, a minimum voltage bias, typically about 2.0 to 2.5 kilovolts (kv) must be applied to the needle. The value of the minimum voltage will vary with hardware configuration and solvent properties of the sample solution such as surface tension, polarity and viscosity. Likewise, there exists a maximum voltage bias, typically about 3.0 to 4.0 kv, beyond which poor or no spectra is obtained from downstream analytical apparatus. This is due to dissociative ionization of the target solute compound due to corona discharge at the needle tip when a sufficiently high voltage which produces the corona discharge is utilized. Alternatively, when the distance between the two electrodes is too small, undesirable arcing occurs between the needle and the downstream counterelectrode which results in breakdown of the electrospray produced. Both of the conditions limit the electrical field that can be utilized to form the electrospray.

It has been proposed by Bruins et al, Anal. Chem., Vol 59, pp 2642-2646 (1987) to alleviate these problems in a pneumatically assisted electrospray system by flushing the needle tip area with gas or gas mixtures which are arc and corona suppressants. This apparatus is sufficiently complex as to require the user to empirically determine optimum condition of gas flow, solvent flow and needle voltage for each sample processed.

Ikonomou et al, Anal. Chem., Vol 63, pp 1989-1991 discloses a needle construction utilized in electrospray or ion spray apparatus. The needle construction comprises an inner silica capillary surrounded by a stainless steel capillary. The solution being converted to an electrospray is passed through the silica capillary. An inert gas such as nitrogen can be passed within a cylindrical space between the silica capillary and the stainless steel capillary. The exposed stainless steel capillary functions as the electrode.

Smithy et al, Anal. Chem. Vol 60, pp 436-441, 1998 discloses a needle construction for an electrospray apparatus similar to that of Ikonomou et al and which includes a silver coating on the outside surface of the stainless steel capillary.

Smith et al, Anal. Chem, Vol 60, pp 1948-1952, 1988 discloses an electrospray needle construction comprising an inner silica capillary surrounded by and spaced apart from an outer stainless steel capillary. An electrically conductive buffer solution is passed between the inner capillary and the outer capillary to form a sheath liquid surrounding the liquid sample which passes through the inner silica capillary.

In all of these needle constructions, the steel capillary is exposed at or near the exit end of the needle construction. The steel capillary functions as the upstream electrode from which the electrical field emanates in cooperation with a downstream counterelectrode. The use of an exposed upstream electrode exposed to the atmosphere severely limits the electrical potential that can be applied thereto without causing undesirable arcing. This limitation, in turn limits the energy that can be applied to the liquid sample emanating from the needle and thereby limits the flow rate of liquid that can be passed through the needle.

It would also be desirable to provide a means for increasing liquid sample flow rate through the needle so that the adverse effect of leakage in the apparatus effecting liquid sample flow would be minimal as compared to the flow rate of liquid sample.

Accordingly, it would be desirable to provide a means which permits utilizing electric fields of greater intensity to form an electrospray that can be utilized with presently available apparatus. The use of such higher intensity fields would permit higher flow rates of sample solution to be processed as compared to flow rates that can be processed with presently available apparatus. In addition, it would be desirable to provide such an apparatus which eliminates the possibility of corona formation.

SUMMARY OF THE INVENTION

The present invention provides a needle apparatus for use in an electrospray apparatus. An electric field is applied to the needle apparatus to effect flow of charge to a liquid stream emanating from the needle apparatus in order to form a spray of fine, electrically charged, liquid droplets.

In contrast to previous needle apparatus used in electrospray apparatus, this invention ensures that the only exposed surface of a conductive material, present in the region of high electric field needed for the formation of an electrospray, is the surface of the sample solution liquid itself as it merges from the tip of the electrospray needle and is electrosprayed.

This is accomplished in two different ways. In the first, a conventional stainless steel hypodermic needle is sheathed by a solid coating of an insulating material such as polytetrafluoroethylene.

In the second, the needle itself is constructed entirely of an electrically insulating material such as a plastic, glass or silica.

BRIEF DESCRIPTION OF THE DRAWINGS

FIG. 1*a* is a schematic view of a first preferred needle apparatus of this invention.

FIG. 1*b* is a schematic view of a second preferred needle apparatus of this invention.

FIG. 2 is a schematic view of a third preferred needle apparatus of this invention.

FIG. 3 shows the electrospray mass spectrum obtained in Example 1.

FIG. 4 shows the electrospray mass spectrum obtained in Example 2.

FIG. 5 shows the electrospray mass spectrum obtained in Example 3.

FIG. 6–6A illustrates the use of the needle apparatus of this invention in conjunction with an analytical apparatus.

DESCRIPTION OF SPECIFIC EMBODIMENTS

Previous needle and electrospray apparatus constructions have failed to sufficiently separate in space the source of electrical charge needed for an electrospray from the region where the high electrical fields needed to generate electrosprays are created. Consequently, they all expose a portion of an electrically conductive element, such as a stainless steel hypodermic needle, are at, or are in close proximity to, the regions where the high electrical fields necessary to achieve electrosprays are generated. This has the effect of limiting the voltage that can be applied to these apparatus since the electrically conductive elements can easily supply abundant quantities of free electrons which can promote and/or sustain the formation of an arc.

In contrast, this invention ensures that the only exposed surface of a conductive material that is exposed to high electric field is the surface of the sample solution liquid itself as it emerges from the tip of the electrospray needle and is electrosprayed.

This can be accomplished in at least two different needle apparatus. The first is illustrated in FIGS. 1*a* and 1*b* through which a liquid stream is flowed. The needle apparatus includes an entrance end for introducing a liquid sample into an inner electrically conductive capillary and an exit end for removing the sample. The electrospray is formed at the exit end. A portion of the inner capillary near the exit end is mostly surrounded by an electrically nonconductive capillary or tube. The exit end of the conductive capillary is positioned upstream of the exit end of the nonconductive tube or capillary. The nonconductive tube or capillary serves to shield, with an electrically insulating material, the outside surface and exit end of the conductive capillary. A voltage is applied to the electrically conductive capillary in order to supply charge to the liquid sample within the capillary. The electrical field generated by the voltage is arranged to be highest at the exit end of the nonconductive tube or capillary by virtue of the geometry of the nonconductive tube exit end and the conductivity of the liquid positioned between the exit end of the conductive capillary and the downstream exit end of the nonconductive tube or capillary. The electrical field is formed between the exit end of the nonconductive tube or capillary and a downstream counterelectrode. Since the outside surface of the conductive capillary is shielded by an insulating material, higher voltage can be utilized without effecting undesirable arcing or corona discharge. This, in turn permits using higher liquid flow rates through the needle apparatus since a greater amount of electrical energy is available to convert the liquid stream to an electrospray.

The nonconductive tube or capillary can be formed of any nonconductive material which is sufficiently mechanically strong as to withstand the mechanical forces normally encountered in an electrospray process. By the term, "nonconductive" is meant a resistivity of greater than about $10^9\Omega$-cm and preferably greater than about $10^{12}\Omega$-cm. Exemplary suitable materials include nonconductive glass compositions, quartz silicate and polymeric compositions such as those based on polyolefins, polytetrafluoroethylenes, polyetheretherketones or the like.

The conductive capillary can be formed of any composition such as stainless steel or the like typically having a resistivity less than about $10^6\Omega$-cm. More generally, for a given applied electrical potential, it is only necessary for the material in question to have a conductivity high enough to provide sufficient flow of charge as is needed to spray a given flow rate of sample solution.

The exit end of the nonconductive tube or capillary is positioned downstream of and remote from the exit end of the conductive capillary. By the term "downstream" as used herein is meant a position remote from a given position in the direction of liquid flow. The distance between the exit end of the conductive capillary and the exit end of the outer nonconductive tube or capillary is such s to minimize or prevent arcing or corona discharge which occurs more easily when an exposed conductive surface is present in the regions of highest electrical field energy at, or closely adjacent to the exit end of the nonconductive tube or capillary. Typical distances between the exit end of the conductive capillary and the exit end of the nonconductive tube or capillary are between about 0.3 cm and 3 cm. When utilizing the needle apparatus of this invention, the liquid flow rates attainable while avoiding arcing or corona discharge are a factor of 10 and higher as compared with a needle apparatus having the same exit end diameter but with the electrically conductive portion of the apparatus exposed to the atmosphere. Typical voltage which can be utilized on the conductive capillary of this invention as compared with a ground voltage for the downstream counterelectrode are between about 800 volts and 27 KV, as compared to between about 3.4 KV and 5.2 KV with conventional needle apparatus.

In the second preferred embodiment, the needle itself is constructed entirely of an electrically insulating material such as polytetrafluoroethylene, polyetheretherketone, glass or silica such that the charge needed to generate an electrospray flows from a physically distant conductive electrode, into the sample solution, and is conducted by the sample solution stream itself to the tip of the insulated needle where electrospray occurs. This scheme is illustrated in FIG. 2. The physical principles that apply to this configuration are the same, i.e. this configuration likewise ensures that the only exposed surface of a conductive material that is exposed to high electric field is the surface of the sample solution liquid itself as it emerges from the tip of the electrospray needle and is electrosprayed.

The arrangements illustrated in FIGS. 1*a*, 1*b* and 2 have the advantage of allowing the application of substantially higher voltages to electrospray needles, such that useful sprays may be generated, without pneumatic, thermal, or ultrasonic assist, or the addition of extra arc suppression gases, at flow rates that can be as much as 10 fold greater than those that it is possible to generate with other electrospray schemes. In addition, the ability to apply higher voltages makes it easier to electrospray solutions of high water content (97% v/v) that are difficult to electrospray with conventional needle apparatus.

Another benefit that may be obtained from scheme outlines in FIG. 1*a* or FIG. 2 are that needle tips of exceedingly fine diameter can be formed such that in one mode of operation, the electrospray can be effected at low voltages with a needle having a small outer diameter in the order of 10 μm to 20 μm. Electrospray can be produced at an applied potential difference as low as about 775 volts between the needle exit and the nearest reference electrode.

Referring to FIG. 1*a*, the needle apparatus 10 includes a plenum 12 for an incoming liquid sample, an upstream inlet 14 of an electrically conductive inner capillary 16 and a downstream liquid outlet 18 of an outer electrically nonconductive tube or capillary 20. A voltage is applied to the inner conductive capillary 16 and the electrical field thereby produced is arranged to be at its highest at downstream outlet 18. The charge for forming an electrospray is provided through inner conductive capillary 16 under the influence of voltage applied thereby. The charge is conducted from capillary 16, through the liquid sample 22, and to the downstream exit 18 such that the charge and field at downstream exit 18 are high enough to cause the exiting liquid sample 20 to break up and form an electrospray 24 without arcing and/or corona discharge.

Referring to FIG. 1*b*, the needle apparatus 30 includes a volume 32 for an incoming liquid sample, an upstream inlet 34 of an electrically conductive capillary 36 and a downstream liquid outlet 38. The capillary 36 is sheathed with an insulating coating 40. A voltage is applied to the conductive capillary 36 and the electrical field thereby produced is arranged to be at its highest at downstream outlet 38. The charge for forming an electrospray is provided through conductive capillary 36 under the influence of voltage applied thereby. The charge is conducted from capillary 36, through the liquid sample 42, and to the downstream exit 38 such that the charge and field at downstream exit 38 are high enough to cause the exiting liquid sample 42 to break up and form an electrospray 44 without arcing and/or corona discharge.

Referring to FIG. 2, the needle apparatus 50 includes a plenum 52 for an incoming liquid sample, an upstream inlet 54 of an electrically insulating capillary 56 and a downstream liquid outlet 58. In this case the plenum 52 must be sufficiently electrically conductive that a voltage applied to the plenum will allow for the transfer of charge into the liquid stream 62. Alternatively another upstream electrode may be provided. A voltage is applied to the plenum 52 and the electrical field thereby produced is arranged to be at its highest at downstream outlet 58. The charge for forming an electrospray is provided through conductive plenum 52 under the influence of voltage applied thereby. The charge is conducted from plenum 52, through the liquid sample 62, and to the downstream exit 58 such that the charge and field at downstream exit 58 are high enough to cause the exiting liquid sample 62 to break up and form an electrospray 64 without arcing and/or corona discharge.

Referring to FIG. 6 a liquid to be electrospray (typically carrying analyte molecules of interest such as from a liquid chromatgraph) flows, in the direction shown by the arrow 26, into one end of the needle 10*a* having an outer nonconductive surface which may be kept at or near electrical ground potential at all times. As it emerges from the other end of this capillary, the liquid is converted to an electrospray, as described above. The end 27, form which the liquid is electrospray, is positioned roughly opposite a conductive plate 30*a* that is electrically isolated by insulating portions 7 from its surrounds and thus maybe set at an arbitrary electrical potential with respect to ground. Plate 30*a* contains an orifice 33. Plate 30*a* also serves as a wall between a region of atmospheric pressure 13 and a region of lower pressure 34*a*. Region 34*a* is maintained at this lower pressure, typically 0.5—3 Torr by the action of a small rotary pump 4. No heat need to be applied to plate 30*a*. Plate 30*a* can be maintained at room temperature. The pressure drop across plate 30*a* causes the ambient atmosphere in region 13 to be drawn through orifice 33. This gas flow, in conjunction with the electric field between the needle 10*a* and plate 30*a* causes some of the electrosprayed droplets and ions to enter orifice 33.

This stream of air, droplets, ions and vapor emerges from orifice 33 into region 34*a* and impinges on a conductive skimmer 18*a* that is electrically insulated from its surrounds by insulated portions 7 and thus may be set at an arbitrary electrical potential with respect to ground. Typically, it operates at a potential such that there exits an electric field between plate 30*a* and skimmer 18*a* that tends to focus charge particles towards skimmer 18*a*. Because of collisions of both charged ion stream components with neutral gas and vapor molecules occur in this region 34*a* as these droplets and solvated ions traverse it on their way to skimmer 18*a* considerable desolvation and ion evaporation occurs such that a usable ion signal can be produced.

Because of the low pressure in this region, the energy of these collisions is considerably affected by the potential difference between plate 30*a* and simmer 18*a*, such that considerable desolvation and ion evaporation occur. The energy of collisions in this region can be controlled by the electrical potential difference between these regions. Indeed, these collisions can be sufficiently energetic that fragmentation of ionized analyte molecules can occur providing useful structural information.

Region 34*a* is bounded by plate 30*a*, skimmer 18*a* wall portion 3. They all can be electrically isolated from each other by insulating portions 7, such that the shape of wall portion 3, and the electrical potential applied to it, can be used to optimize charged particle transmission. It is, however, also possible for wall portion 3 to be electrically part and/or mechanically part of either plate 30a or skimmer 18a.

Some portion of the ions and droplets arriving at skimmer 18a traverse the orifice 19 at its apex and enter region 20a. Region 20a is ideally separated from the region 21 containing the mass spectrometer 22a, and each region is usually separately pumped, but this is not mandatory. In other embodiments, regions 20a and 21 need not be separated. In either case, ion optics 24a are contained in region 20a that serve to focus ions, emerging into region 20a (via orifice 19), onto the entrance aperture 25 of the mass analyzer 22a. Typically this is a quadrupole mass spectrometer, an ion trap, an ion mobility spectrometer, a time-of-flight spectrometer or a magnetic sector mass spectrometer. These ion optics can also be designed such that they can also serve to ionize neutral gas molecules, introduced into region 20a through leak valve 23, by conventional electron impact ionization.

The following examples illustrate the present invention and are not intended to limit the same.

EXAMPLE 1

Figure 1B:
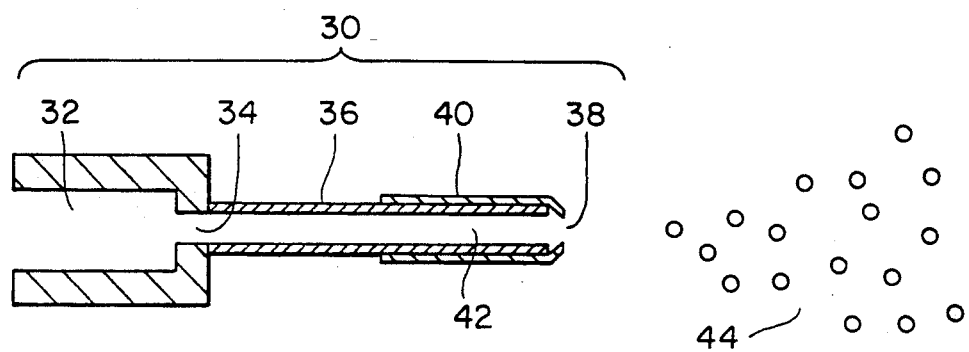
Figure 3:
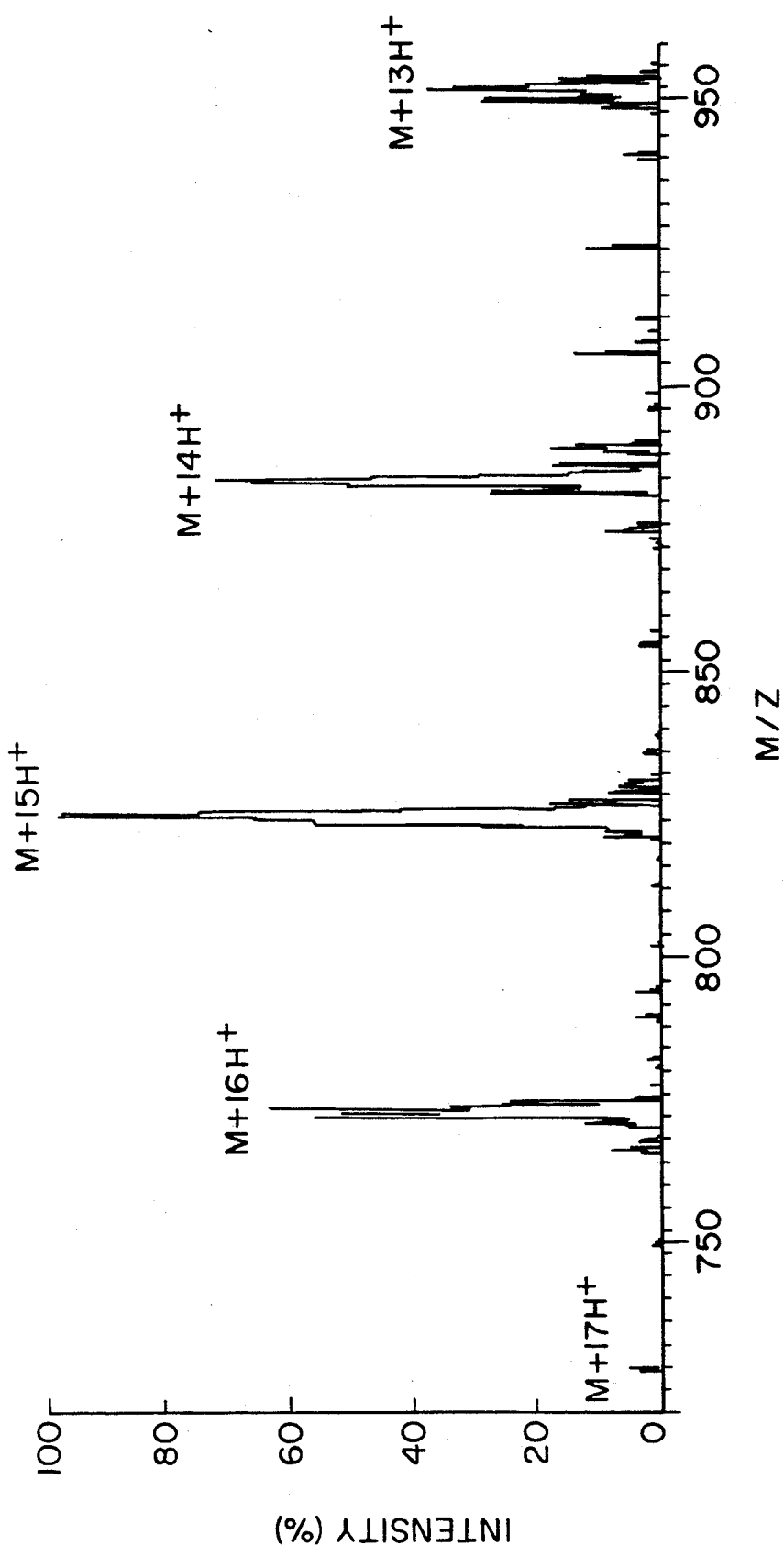

This example illustrates the high flow rate capability of this invention. Utilizing the apparatus of FIG. 1 wherein the inner capillary is formed of stainless steel having an inner diameter of 0.25 mm and an outer diameter of 0.5 mm and an outer capillary formed of polytetrafluoroethylene having a thickness of about 0.10 mm, the following experiment was conducted. A 5 $\mu$M solution of horse heart cytochrome C in a methanol/water/acetic acid (47/476, v/v/v) solvent was electrosprayed at a flow rate of 20 $\mu$L/min. A voltage of 18 KV relative to a downstream grounded counterelectrode was applied. The resultant electrospray mass spectrum was obtained with a quadrupole mass spectrometer and is shown in FIG. 3. The molecular weight calculated for this molecule from this mass spectrum is 12,358 +/−3 Daltons and the theoretical mass is 12,360.8 Daltons. The maximum flow rate obtained without arcing or corona discharge with a conventional needle apparatus with a conductive capillary exposed to the atmosphere was about 4 $\mu$L/min.

EXAMPLE 2

Figure 2:
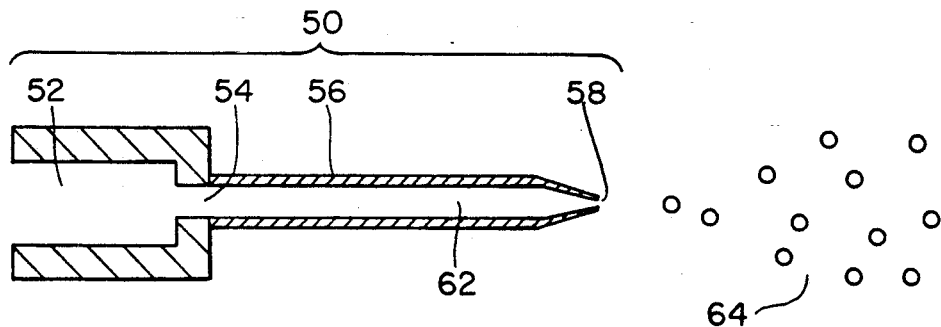
Figure 4:
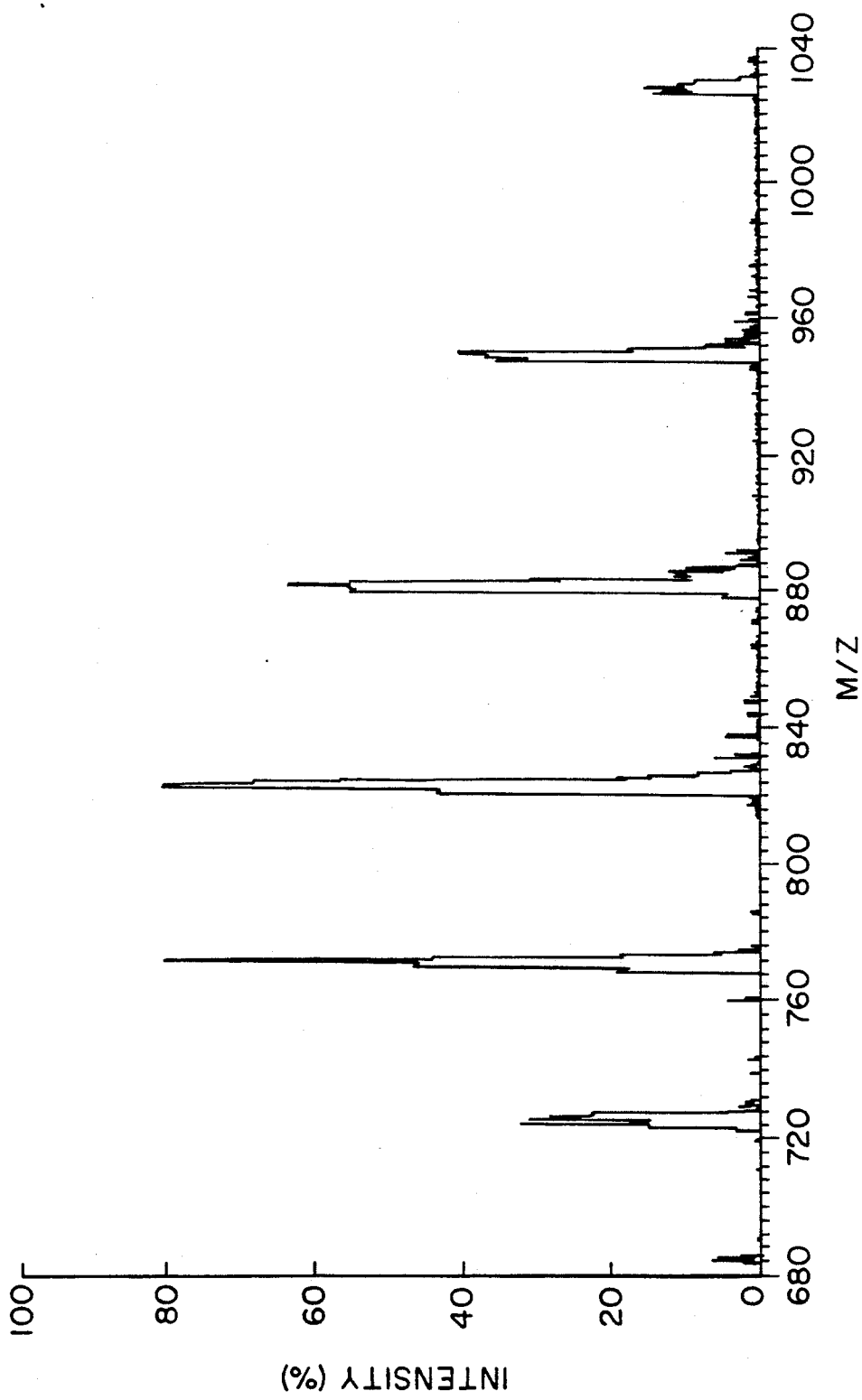

This example illustrates the low voltage capability of this Invention. Utilizing the apparatus of FIG. 2 wherein the capillary is found of a pulled glass micropipette having a tip inner diameter of 0.001 cam and a tip outer diameter of 0.0017 cm the following experiment was conducted. A 5 $\mu$M solution of horse heart cytochrome C in a methanol/water/acetic acid (47/47/6, v/v/v) solvent was electrosprayed at a flow rate of 1 $\mu$L/min. A voltage of 1.3 KV relative to the nearest downstream electrode was applied. The resultant electrospray mass spectrum was obtained with a quadrupole mass spectrometer and is shown in FIG. 4.

EXAMPLE 3

Figure 5:
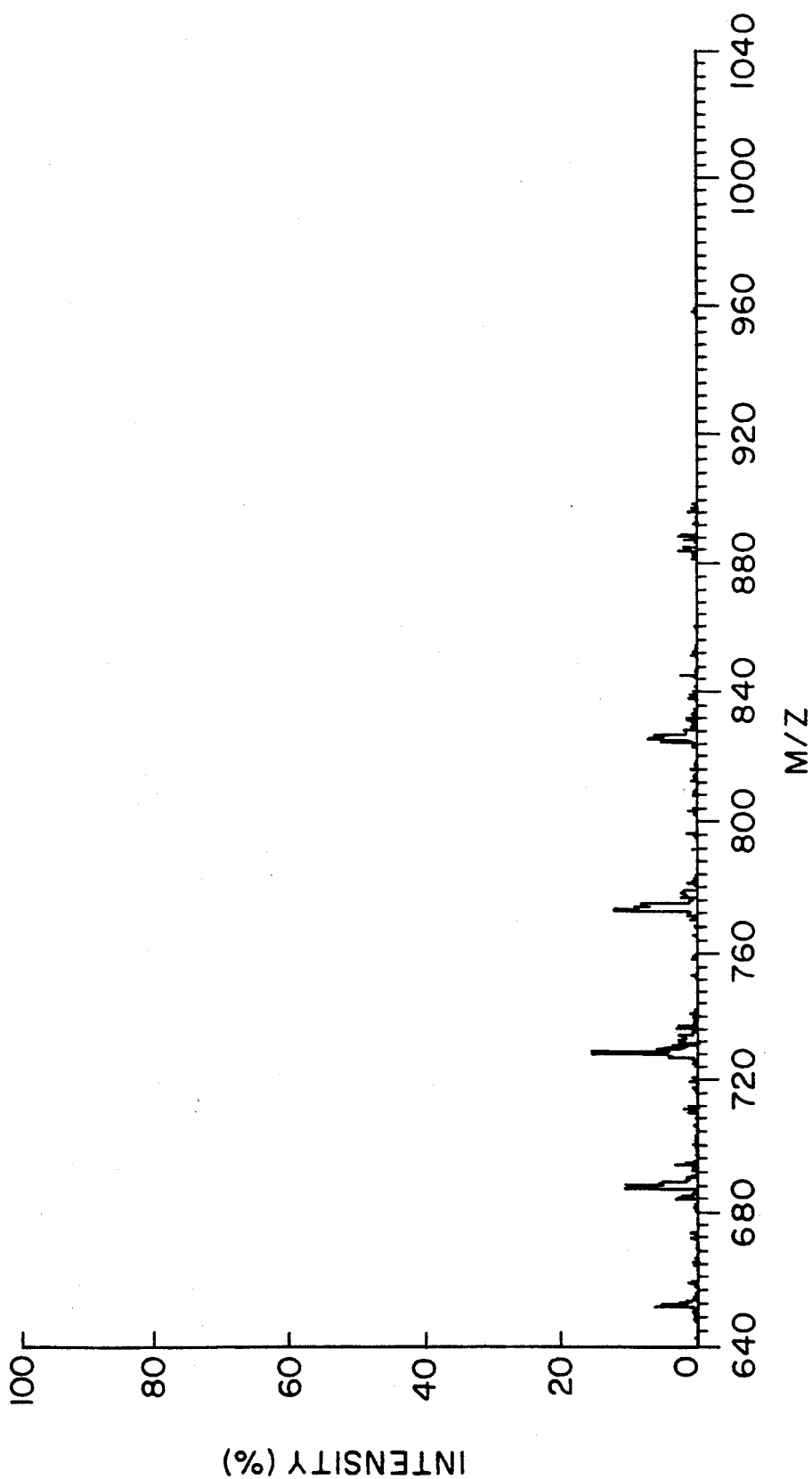
Figures 6, 6A:
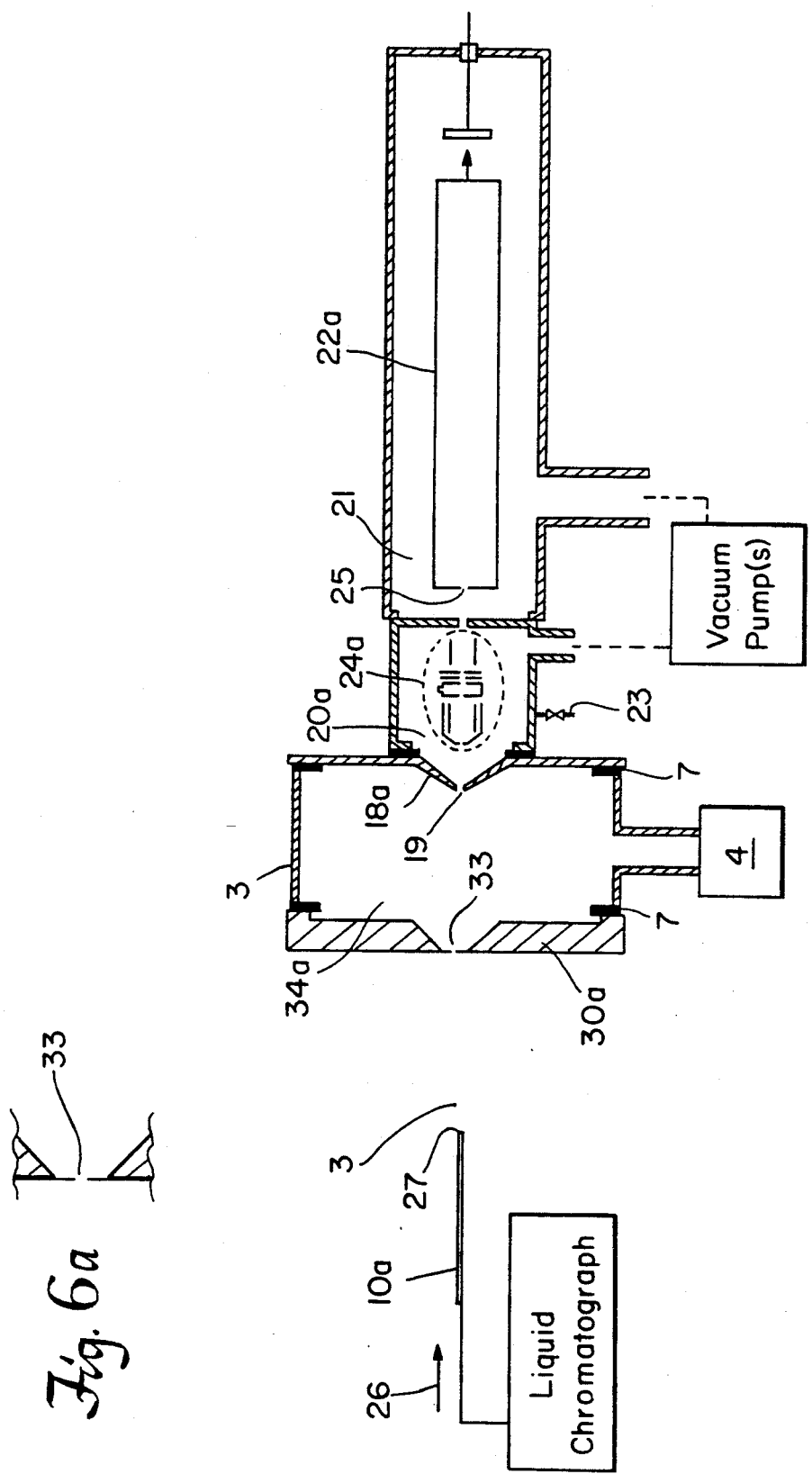

This example illustrates the capability of this invention to electrospray high water content solutions. Utilizing the apparatus of FIG. 2 wherein the capillary is formed of a pulled glass micropipette having a tip inner diameter of 0.01 cm and a tip outer diameter of 0.0175 cm the following experiment was conducted. A 5 $\mu$M solution of horse heart cytochrome C in a water/acetic acid (97/3, v/v) solvent was electrosprayed at a flow rate of 2 $\mu$L/min. A voltage of 4.8 KV relative to the nearest downstream electrode was applied. The resultant electrospray mass spectrum was obtained with a quadrupole mass spectrometer and is shown in FIG. 5.

We claim:

1. A needle apparatus for converting a liquid into an electrospray comprising electrically charged liquid droplets, said needle apparatus having an entrance end and an exit end, means for introducing said liquid into said entrance end, an inner electrically conductive capillary in liquid communication with said entrance end having a liquid outlet, an outer electrically nonconductive tube surrounding said electrically conductive capillary and said liquid outlet of said electrically conductive capillary to electrically insulate said liquid outlet from atmosphere surrounding said needle apparatus.

said nonconductive tube having an liquid outlet comprising said exit end and means for effecting an electrical potential on said electrically conductive capillary.

2. The needle apparatus of claim 1 wherein said electrically nonconductive tube contacts an outside surface of said electrically conductive capillary.

3. The needle apparatus of any one of claims 1, or 2 wherein said outer electrically nonconductive tube comprises a nonconductive polymeric composition.

4. The needle apparatus of any one of claims 1, or 2 wherein said outer nonconductive tube comprises a silica composition.

5. A needle apparatus for converting a liquid into an electrospray comprising electrically charged liquid droplets, said needle apparatus having an entrance end and an exit end, means for introducing said liquid into said entrance end, an electrically nonconductive capillary in liquid communication with said entrance end, said electrically nonconductive capillary having a liquid outlet comprising said exit end and means for effecting an electrical potential on liquid at said entrance end of said electrically nonconductive capillary.

6. The needle apparatus of claim 5 wherein said electrically nonconductive capillary comprises a nonconductive polymeric composition.

7. The needle apparatus of claim 5 wherein said electrically nonconductive capillary comprises a silica composition.

8. The apparatus of any one of claims 1, 2, 5, 6 or 7 which includes means from analyzing an electrospray emerging from said exit end.

9. The apparatus of claim 3 which includes means for analyzing an electrospray emerging from said exit end.

10. The apparatus of claim 4 which includes means of analyzing an electrospray emerging from said exit end.

* * * * *